United States Patent
Hamalainen et al.

(10) Patent No.: US 10,663,461 B2
(45) Date of Patent: May 26, 2020

(54) SCREENING METHOD

(75) Inventors: Markku Hamalainen, Uppsala (SE);
Hakan Roos, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 859 days.

(21) Appl. No.: 13/990,759

(22) PCT Filed: Nov. 29, 2011

(86) PCT No.: PCT/SE2011/051444
§ 371 (c)(1),
(2), (4) Date: May 30, 2013

(87) PCT Pub. No.: WO2012/074473
PCT Pub. Date: Jun. 7, 2012

(65) Prior Publication Data
US 2013/0252846 A1     Sep. 26, 2013

(30) Foreign Application Priority Data
Nov. 30, 2010 (SE) ...................................... 1051263

(51) Int. Cl.
| | |
|---|---|
| *G01N 33/48* | (2006.01) |
| *G01N 33/543* | (2006.01) |
| *C40B 30/04* | (2006.01) |
| *G06G 7/58* | (2006.01) |
| *G16C 20/20* | (2019.01) |
| *G16B 35/00* | (2019.01) |
| *G16C 20/60* | (2019.01) |

(52) U.S. Cl.
CPC ............ *G01N 33/543* (2013.01); *C40B 30/04* (2013.01); *G01N 33/54373* (2013.01); *G16B 35/00* (2019.02); *G16C 20/20* (2019.02); *G16C 20/60* (2019.02)

(58) Field of Classification Search
None
See application file for complete search history.

(56) References Cited

U.S. PATENT DOCUMENTS

| | | |
|---|---|---|
| 2005/0123902 A1 | 6/2005 | Meneses et al. |
| 2009/0143285 A1 | 6/2009 | Sueoka et al. |

FOREIGN PATENT DOCUMENTS

| | | |
|---|---|---|
| WO | WO 03/005890 | 1/2003 |
| WO | WO 2009/025680 | 2/2009 |
| WO | WO 2011/000566 | 1/2011 |

OTHER PUBLICATIONS

Workshop Series—Strategies for Working With Smaoll Molecules, Protocol for Measureing Small Molecule Interations Using Biacored Jan. 1, 2002.
Sandblad et.al. Analytical Chemistry, vol. 81, No. 9, May 1, 2009 pp. 3551-3559.

*Primary Examiner* — Eric S Dejong
(74) *Attorney, Agent, or Firm* — Hanley, Flight and Zimmerman, LLC

(57) ABSTRACT

A method of screening a plurality of fluid samples for the presence of species capable of specifically binding to a binding partner immobilized on a sensing surface of a sensor is disclosed. The method comprises contacting each sample with the sensing surface and a reference surface, and subjecting the sensing surface responses obtained for all samples to a computational process which comprises fitting al responses to a model equation for the relationship between a response at the sensing surface and the corresponding response at the reference surface. In an iterative process residuals above a pre-determined threshold value are removed, the model equation is adjusted, and all remaining samples are refitted to the adjusted model equation until the model equation at least substantially converges. Residuals above the predetermined threshold value are considered as species specifically binding to the binding partner. The method may be computer-implemented, and a computer program product therefore comprises instructions for causing a computer to perform the computational process.

16 Claims, 15 Drawing Sheets

SCREENING METHOD

CROSS-REFERENCE TO RELATED APPLICATIONS

This application is a filing under 35 U.S.C. 371 of international application number PCT/SE2011/051444, filed Nov. 29, 2011, published on Jun. 7, 2012 as WO 2012/074473, which claims priority to patent application number 1051263-0 filed in Sweden on Nov. 30, 2010.

FIELD OF THE INVENTION

The present invention relates to a method of screening a pool of chemical compounds for capability of specifically binding to a desired binding partner or receptor, particularly screening of molecular libraries, such as drug libraries.

BACKGROUND OF THE INVENTION

Optical biosensors based on surface plasmon resonance (SPR) are today widely used for analyzing a wide range of biological and chemical interactions. SPR biosensors allow the determination of the affinity and kinetics of molecular interactions in real time without the need for a molecular tag or label. Analytes, or ligands, in a solution are contacted with a sensing surface with immobilized binding partner, or receptor. Binding of analyte to surface-bound binding partner alters the refractive index at the sensing surface, and this refractive index change can be monitored to measure accurately the amount of bound analyte, its affinity for the receptor and the association and dissociation kinetics of the interaction. Commercial SPR biosensor systems are available which permit a high degree of automation and parallelization, and may therefore be used for high throughput screening assays.

However, a negative feature of SPR biosensors is their sensitivity to the optical properties of the samples. While such bulk effects as well as effects of signal drift and non-specific binding are usually corrected for by the use of a reference surface, the sample bulk effect may in some instances be so large that they can mask the specific binding signal. This is, for example, the case when studying interactions of small molecules, i.e. of low molecular weight, such as in so-called drug libraries, which as a result of their limited solubility in aqueous solutions usually have to be dissolved in buffers containing organic solvents, typically dimethyl sulfoxide (DMSO). DMSO has a high refractive index, and small differences in concentration will therefore induce large increases in response signal that have to be subtracted.

Today, this is variance is corrected for by performing a rather sophisticated and laborious calibration procedure, often referred to as solvent correction, involving the creation of a calibration curve by running negative controls with varying DMSO contents.

It is an object of the present invention to provide a method for screening compounds in drug libraries and the like which does not require a separate solvent correction step involving separate runs with calibration solution.

SUMMARY OF THE INVENTION

According to the present invention, the above-mentioned object is achieved by running a screening procedure with the biosensor without any solvent calibration, and instead treating the measurement results according to a computational procedure, or algorithm, of regression analysis type, which comprises providing a regression model, or equation, for the relationship between the response at the target surface and the response at the reference surface, and in an iterative fitting process eliminating specific binders and adjusting the regression model until all binders have been eliminated and the regression model has (at least substantially) converged. The converged regression model will then describe the bulk effect to solvent variation in samples, and the residuals from the fit of all samples to the regression model will represent the true binding from the compounds.

The above approach is, however, not limited to the elimination of solvent bulk effects, but may generally be applied when a reference surface or signal in some form is used (and, typically, more non-binders than binders are expected) to eliminate any varying effect which does not correlate with the true specific binding.

Likewise, while the invention is primarily described herein with regard to SPR biosensors, it is not limited to the use with such sensors. On the contrary, the method of the invention is applicable to all types of sensors experiencing similar problems with, for example, non-specific bulk or other effects of varying type.

In one aspect, the present invention therefore provides a method of screening a plurality of fluid samples for the presence of species capable of specifically binding to a binding partner immobilized on a sensing surface of a sensor, which method comprises contacting each sample with the sensing surface and a reference surface, and subjecting the sensing surface responses obtained for all samples to computational process which comprises fitting all responses to a model equation for the relationship between a response at the sensing surface and the corresponding response at the reference surface in an iterative process which comprises removing residuals above a pre-determined (positive) threshold value, adjusting the model equation, and refitting all remaining sample responses to the adjusted model equation until the model equation at least substantially converges, wherein residuals above said pre-determined threshold value are considered as species specifically binding to the binding partner.

Usually, also residuals below a pre-determined negative threshold value are removed in the iterative process which relate to species binding to the reference surface.

The reference surface may in one embodiment be a surface without immobilized binding partner. In another embodiment the reference surface has an immobilized binding partner the binding site of which has been blocked.

In a typical embodiment, the sample contains a component giving rise to a non-specific bulk effect, especially a solvent, and the at least substantially converged model equation is then considered as defining the non-specific bulk effect.

Other preferred embodiments are set forth in the dependent claims.

In another aspect, the present invention provides a computer program product comprising instructions for performing the computational process of the method aspect above.

A more complete understanding of the present invention, as well as further features and advantages thereof, will be obtained by reference to the following detailed description and the accompanying drawings.

DETAILED DESCRIPTION OF THE INVENTION

Figure 1:
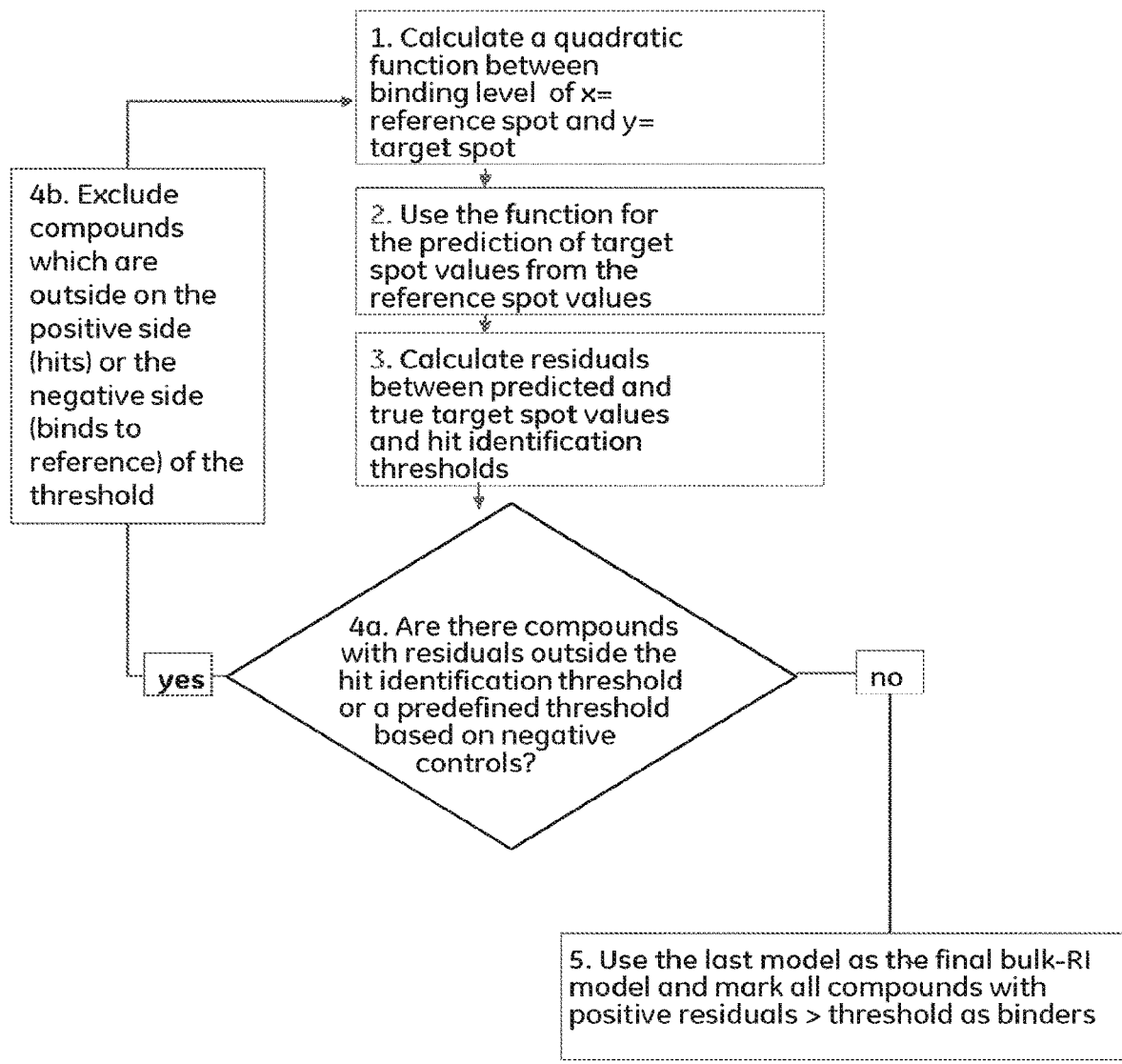
FIG. 1 is a block diagram of an algorithm for performing a screening method according to the invention.

Unless defined otherwise, all technical and scientific terms used herein have the same meaning as commonly understood by a person skilled in the art related to this invention. Also, the singular forms "a", "an", and "the" are meant to include plural reference unless it is stated otherwise As mentioned above, the present invention provides an improvement in the screening of drug libraries and the like. In brief, the invention simplifies and speeds up the performing of screening assays with SPR biosensors and other sensors with which correction for large varying non-specific bulk effects, such as DMSO calibration, is usually required. According to the invention, this is accomplished by subjecting the sample responses from the screening assay to an iterative fitting procedure of regression analysis type to a model equation which successively eliminates binders (i.e. hits) to eventually produce an equation defining the bulk effect.

Before describing the invention any further, however, the concept of biosensors, and especially SPR sensors, will be briefly described.

A biosensor is typically based on label-free techniques, detecting a change in a property of a sensor surface, such as mass, refractive index or thickness of the immobilized layer.

Typical sensors for the purposes of the present invention include, but are not limited to, mass detection methods, such as optical methods and piezoelectric or acoustic wave methods, including e.g. surface acoustic wave (SAW) and quartz crystal microbalance (QCM) methods. Representative optical detection methods include those that detect mass surface concentration, such as reflection-optical methods, including both external and internal reflection methods, which may be angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors, external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaking mode spectroscopy, reflective interference spectroscopy (RIfS), transmission interferometry, holographic spectroscopy, and atomic force microscopy (AFR).

Among the biosensors mentioned above may especially be mentioned optical evanescent wave-based sensors including surface plasmon resonance (SPR) sensors, frustrated total reflection (FTR) sensors, and waveguide sensors, especially SPR biosensors.

Several SPR based biosensor systems are commercially available today. Exemplary such SPR-biosensors include the flow-through-cell-based Biacore® systems (GE Healthcare, Uppsala, Sweden) and ProteOn™ XPR system (Bio-Rad Laboratories, Hercules, Calif., USA) which use surface plasmon resonance for detecting binding interactions between molecules, "analytes", in a sample and molecular structures, "ligands", immobilized on one or more sensing surfaces or spots.

The phenomenon of surface plasmon resonance, or SPR, is well known. Suffice it to say that SPR arises when light is reflected under certain conditions at the interface between two media of different refractive indices, and the interface is coated by a metal film, typically silver or gold. In the Biacore™ system, the media are the sample and the glass of a sensing surface provided by a sensor chip which is contacted with the sample through a microfluidic flow system. The metal film is a thin layer of gold on the chip surface supporting a ligand for an analyte in the sample. SPR causes a reduction in the intensity of the reflected light at a specific angle of reflection. This angle of minimum reflected light intensity, the "SPR angle", varies with the refractive index close to the surface on the side opposite from the reflected light, in the Biacore™ system the sample side. As analyte in a sample solution contacted with the chip surface binds to the immobilized ligand, the refractive index near the chip surface increases, leading to a shift in the SPR angle. When the sample solution is replaced by a solution without analyte, the analyte-ligand complex dissociates and the refractive index decreases, resulting in the SPR angle shifting back.

As sample is passed over the sensing surface, the progress of binding of analyte to immobilized ligand, as detected by the shift in SPR angle, directly reflects the rate at which the interaction occurs. Injection of sample is usually followed by a buffer flow during which the detector response reflects the rate of dissociation of the complex on the surface. A typical output from the system is a graph or curve describing the progress of the molecular interaction with time, including an association phase part and a dissociation phase part. This binding curve recording the shift in the SPR angle as a function of time, and which is usually displayed on a computer screen, is often referred to as a "sensorgram". The angular shift is measured in response units (RU), 1 RU being equal to a $10^{-6}$ change in refractive index. Usually, the sample also passes a reference surface without immobilized ligand for referencing away non-specific binding events and other effects unrelated to specific binding.

With the Biacore® and analogous SPR-based sensor systems it is thus possible to determine in real time without the use of labeling, and often without purification of the substances involved, not only the presence and concentration of a particular molecule, or analyte, in a sample, but also additional interaction parameters, including kinetic rate constants for association (binding) and dissociation in the molecular interaction as well as the affinity for the surface interaction.

Now back to the invention. As mentioned above, compounds in so-called drug libraries are typically small molecules with limited solubility in aqueous solutions and therefore have to be stored in buffer containing an organic solvent, usually DMSO (dimethyl sulfoxide).

As mentioned above, the SPR signal reflects changes in refractive index (RI) as a result of increases in mass at the sensor surface. If the injected sample medium has a RI different from that of the running buffer an additional signal is obtained known as the "bulk refractive index", also referred to as a solvent effect. The solvent effect can usually be removed by subtracting the reference surface from the active surface when the solvent effect is small.

However, in most assays for small molecules where DMSO, which in itself has a relatively high refractive index, is used as a solvent, the subtraction of the reference surface or spot will usually not eliminate the contribution of the solvent to the measured response because a higher DMSO bulk response may be obtained from the reference surface. This is due to bulk solution being excluded from the volume occupied by ligand molecules on the active sensing surface, and the bulk contribution to the relative response will therefore be smaller than that on the reference surface. While this difference is small, it may be of the same order of magnitude as the responses expected from binding of low molecular weight compounds.

Basically, so-called solvent correction is required when the expected analyte responses are low, the ligand is a macromolecule immobilized at a high density at the surface, and the absolute bulk response is high and is subject to variations between sample solutions. These circumstances commonly arise when working with low molecular weight analytes, such as drug candidates. The combination of these three factors results in variations in the magnitude of the excluded volume effect that are significant in relation to the measured analyte response.

In drug discovery and development work, for example, the analytes are usually small molecules that give correspondingly low responses (typically of the order of 50-100 RU or less). High levels of immobilized ligands (several thousands RU) are used to maximize the analyte response. Addition of DMSO to samples and buffers gives a high bulk response. A difference of 1% in DMSO concentration corresponds to a difference of about 1200 RU in bulk response, so that small variations in DMSO concentrations, which are unavoidable when preparing a large number of diverse samples, may thus lead to significant differences in bulk response between samples.

The necessary solvent correction requires a rather sophisticated calibration procedure involving the creation of a DMSO calibration curve by running negative controls with varying DMSO contents, and plotting the signal on the reference surface against the reference-subtracted signal on the active or specific surface. Correction factors are calculated by inserting the signal on the reference surface as x-value in to the equation obtained from linear regression of the calibration curve. The corresponding reference-subtracted y-value is the correction factor.

It is readily seen that such a laborious calibration procedure involving separate runs with calibration solution will slow down the assay process. This artificial calibration is additionally disadvantageous in that the artificial calibration solutions will not fully reflect the environment of the samples which often give rise to zero baseline shift effects, i.e. non-binders (negatives) will get a signal which significantly deviates from zero.

According to the present invention, solvent correction as described above may be avoided by instead subjecting the signal responses obtained in small-molecule screening applications, such as drug-screening, to a computational procedure, or algorithm, involving regression analysis and which uses the non-binding samples for the elimination of bulk refractive index effects.

Regression analysis, which is a well-known statistical method for analysing the relationship between a dependent variable y and one or more independent x-variables, has a variety of applications in empirical science and technology. In regression analysis, obtained x-data are fitted to a regression model $y=f(x)$ which may be more or less complicated. A simple regression model is, for instance, a linear regression equation where y depends linearly on x.

The term "residual" denotes the difference between the observed value of the dependent variable and the predicted value, or in other words the deviation of a data point from the fitted curve. Both the sum and the mean of the residuals are equal to zero.

A "residual plot" is a graph that shows the residuals on the vertical axis and the independent variable on the horizontal axis. If the points in a residual plot are randomly dispersed around the horizontal axis, a linear regression model is appropriate for the data otherwise, a non-linear model is more appropriate.

Data points that diverge from the overall pattern and have large residuals are referred to as "outliers." Outliers limit the fit of a regression equation to the data.

The goodness of a fit is indicated by the coefficient $R^2$ which is a statistical measure of how well the regression line approximates the data points. An $R^2$ of 1.0 indicates a perfect fit to the data, whereas an $R^2$ of 0 indicates no fit at all.

The algorithm of the invention starts with all samples from a screening campaign to define an initial sample internal calibration equation. In an iterative process binders are then eliminated from the calibration, and new bulk equations are calculated and applied to the entire set of samples. After the algorithm has converged, the equation based on non-binders describes the bulk effect due to DMSO variation in samples, and the residuals from the fit of all samples to the equation describe the true binding of compounds.

FIG. 1 shows a schematic block diagram of an exemplary algorithm for use according to the invention to process experimental data from a screening process for identifying binders, or hits, in a small molecule library.

In a first step, a regression model, below sometimes referred to a as bulk-RI model, is defined for the binding level between a target spot (y) and a reference spot (x) for all samples. The regression model is preferably non-linear, for example a quadratic function $y=ax^2+bx+c$, where a, b and c are constants.

In a second step, the regression model is used for the prediction of the target spot values from the reference spot values by fitting the experimental data to the regression model.

In a third step, residuals between predicted and true target spot values and hit identification thresholds are calculated. The average residuals and the standard deviation (SD) of the residuals are used for forming (i) a hit identification threshold (e.g. "average+2 SD" or "average+3 SD"), as well as (ii) a threshold for identification of compounds which bind to the reference surface (e.g. "average−2 SD" or "average−3 SD").

In a fourth step, it is determined if there are compounds with residuals outside the thresholds defined in the third step.

If the answer is yes, the compounds outside the threshold limits, either on positive side (hits) or the negative side (bind to reference) of the threshold are excluded and the first to fourth steps are repeated in an iterative process successively eliminating binders until the answer in the fourth step is no, all binding compounds then having been eliminated from the bulk-RI model. The model has thus converged, i.e. it is based on non-binders and is not improved based on the R2-value (>0.9999). The model equation will then describe the bulk-RI effect due to DMSO variation in samples.

In a fifth step, finally, the last model is used as the final bulk-RI model and all compounds eliminated due to positive residuals larger than threshold values are considered as binders. Binders may be identified successively as residuals are removed in the iterative process, or, preferably, in a final run of all samples against the last model.

It is understood that when the number of binders is relatively small and the vast majority of the compounds in the sample are negatives, the compounds which bind to the target will be indentified already in the first rounds and the remaining samples can then be used for modelling the bulk-RI effect.

The number of compounds identified as binders will vary depending on the statistical threshold used. A 95% threshold (2 SD) will classify borderline compounds as binders but at the same time also give a purer bulk-RI model (no binders included). Higher thresholds (3 or 4 SD, i.e. 99 pr 99.9%), on the other hand, will give a lower number of hits but will increase the risk of producing an increased number of false negatives and also include more binders to the model. Such inclusion of weak binders to the bulk-RI model will automatically decrease the signal of all compounds. Optionally, different thresholds may be used in different runs of the iterative binder elimination process.

As apparent form the above, also negative binders may be identified, i.e. which bind stronger to the reference surface than to the target.

While statistical thresholds are used in the algorithm outlined above, it is also possible to use other thresholds instead of, or in combination, with statistical thresholds. For example, thresholds may be calculated from known negative controls and/or positive controls. The selected thresholds may be constant throughout the iterative fitting procedure or varied between iterations.

While not implemented into the algorithm shown in FIG. 1, it is preferably checked that the compounds eliminated from the model equation are not eliminated due to a large positive/negative bulk-RI effect. This risk may be eliminated by including a few control samples covering the ends of the bulk-RI interval when running the screen.

A factor which will influence the quality of bulk-RI elimination is drift which may be caused by (i) variation related to storage and preparation (such as evaporation from non-sealed plates during plate preparation with robot, how well the plates are sealed and storage time in the instrument), (ii) bleeding of target protein (and/or reference) from the surfaces, and (iii) precipitations. Bleeding and storage in the instrument will often give a systematic variation in bulk-RI which can be modelled as a function of cycle number (1 sample=1 cycle), and may therefore be included into the algorithm, whereas other types of changes may be more difficult to identify.

At least in situations with drift caused by bleeding from the surface, the quality of data may be increased by running the algorithm in a sequential manner using a "moving window" for the analysis cycles included. For example, a 300 cycles run can be divided into 6 parts of 50 cycles (cycle 1-50, 51-100 . . . etc).

The procedure outlined above is not limited to the elimination of solvent effects, such as bulk refractive index effects, but may be used in any situation where there is a varying effect which does not correlate with the true specific signal/binding, including e.g. also detector non-linearities.

The method steps according to the algorithm outlined above may conveniently be implemented by software run on an electrical data processing device, such as a computer. Such software may be provided to the computer on any suitable computer-readable medium, including a record medium, a read-only memory, or an electrical or optical signal which may be conveyed via electrical or optical cable or by radio or other means. Such software may preferably include several significance levels (e.g. 95%, 99%, 99.9%) for the hit selection threshold from which the selection of hit threshold is left to the user.

A characteristic feature of the method of the invention is that the bulk-RI elimination and the hit-identification processes are performed simultaneously.

In the following experimental part, the invention will be described and illustrated in more detail, by way of example only, by means of some non-limiting Examples.

EXAMPLES

Experimental Data

The experimental data used in the Examples below are taken from a screen performed on a fragment library.

"Fragment-based drug design" is nowadays an accepted approach for the discovery and development of therapeutic compounds. Fragments occupying different parts of the binding site of a target molecule can be synthetically linked into new compounds which often have much higher affinities than can what be expected from a simple combination of their individual affinities.

The fragment library used was purchased from Maybridge (part of Thermo Fisher Scientific) and consisted of 500 compounds with molecular weights in the range 94-291 Da.

DMSO was added to the vials to give 100 mM solutions. After removal of DMSO-insoluble substances (a total of 23), the remaining solutions were aliquoted to six 96-well microtiter plates (80 substances per plate) and diluted with DMSO to 50 mM.

A Biacore® A100 instrument (GE Healthcare, Uppsala, Sweden) was used for the screen. The Biacore® A100 has four flow channels arranged in a linear array with five detection spots in each channel. The spots can be hydrodynamically addressed by changing the flow rate from two inlet channels, one with sample and one with buffer. The output from the instrument is a "sensorgram" which is a plot of detector response (measured in "resonance units", RU) as a function of time. (1 RU≈$10^{-6}$ change in refractive index). An increase of 1000 RU corresponds to an increase of mass on the sensor surface of approximately 1 ng/mm$^2$.

As sensor chip was used Sensor Chip CM5 series S (GE Healthcare, Uppsala, Sweden) which has a gold-coated surface with a covalently carboxymethyl-modified dextran polymer hydrogel.

Using the Biacore® A100 instrument, the fragment library was screened against gluthathione S-transferase (GST), carbonic anhydrase (CA) as well as thrombin and its diisopropyl fluorophosphates-blocked derivative (thrombin-DFP) as targets. As positive controls for CA and thrombin were used 30 µM furosemide and 2 µM DAPA (dansylarginine N-(3-ethyl-1,5-pentanediyl)amide), respectively. Running buffer was used as the negative control.

GST, CA, thrombin and thrombin-DFP were immobilized on spots 1, 2, 4 and 5, respectively, of all four flow cells. All measurements were performed at 25° C. with PBS-P+, 5% DMSO, as running buffer at a flow rate of 30 µl/min. Test substances and furosemide were injected in a cycle with a contact time of 30 s and dissociation time of 30 s followed by an extra wash with 50% DMSO and carry-over. Due to the slow dissociation of the thrombin-DAPA complex, a longer dissociation time (900 s) was used in the DAPA injection cycle. The runs were started with three start-up cycles (running buffer injection) followed by a solvent correction, negative control (running buffer) and furosemide. Solvent correction was then repeated after every 60 cycles and furosemide and negative control after 30 cycles. DAPA was injected at the start of the run. Untreated surface (spot 3) was used as a reference for GST, CA and thrombin. In addition, thrombin-DFP was used as a reference for thrombin.

Parts of the analytical data produced in the runs described above were used in the Examples below.

Example 1

Simple Regression Model

Figure 2:
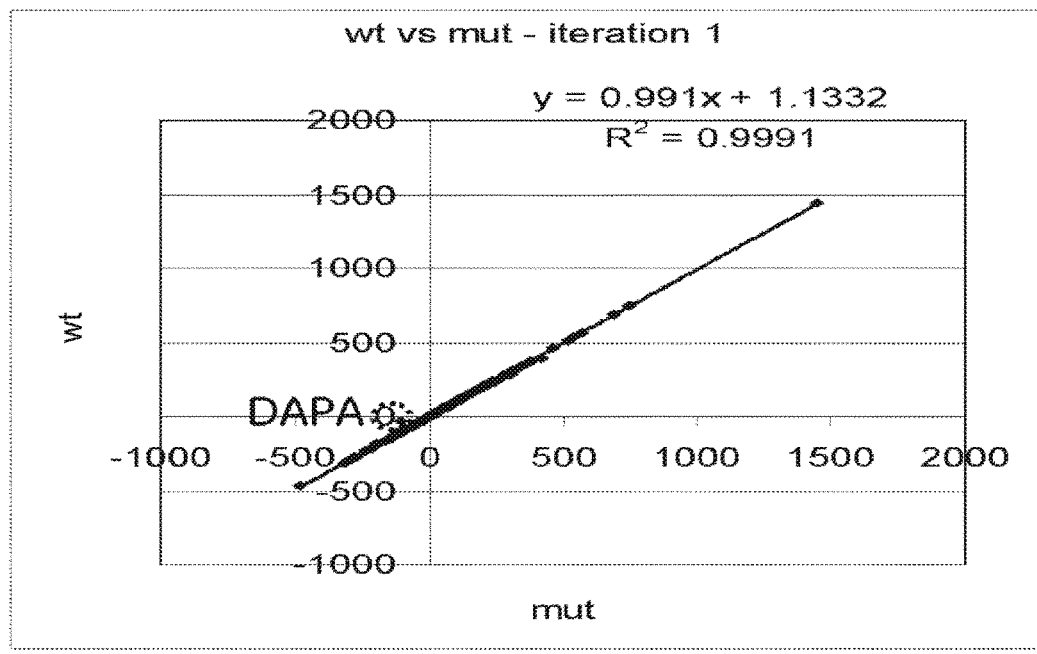
FIG. 2 is a set of diagrams (a) to (f) showing results obtained when a simple linear model is used in the algorithm outlined in FIG. 1. Diagram (a) is a plot of target vs. reference spot after the first fitting to the model using all samples, and (b) is a plot of calculated residuals vs. cycle no. (1 cycle=1 sample) for the fitting with all samples. Diagram (c) is a corresponding plot to that in (a) for a reiterated fitting after removal of binders, (d) is a residual plot after the reiterated fitting, and (e) is corresponding residual plot obtained with an ordinary DMSO calibration. Diagram (f) is a plot of DMSO calibration vs. internal calibration according to the invention.
Figure 2:
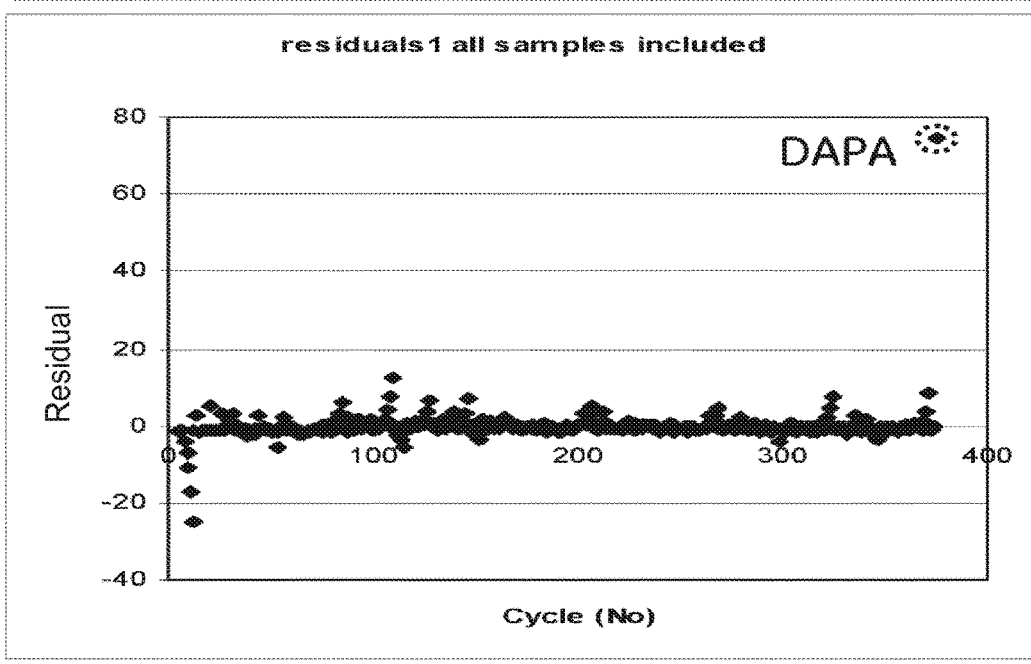
Figure 2:
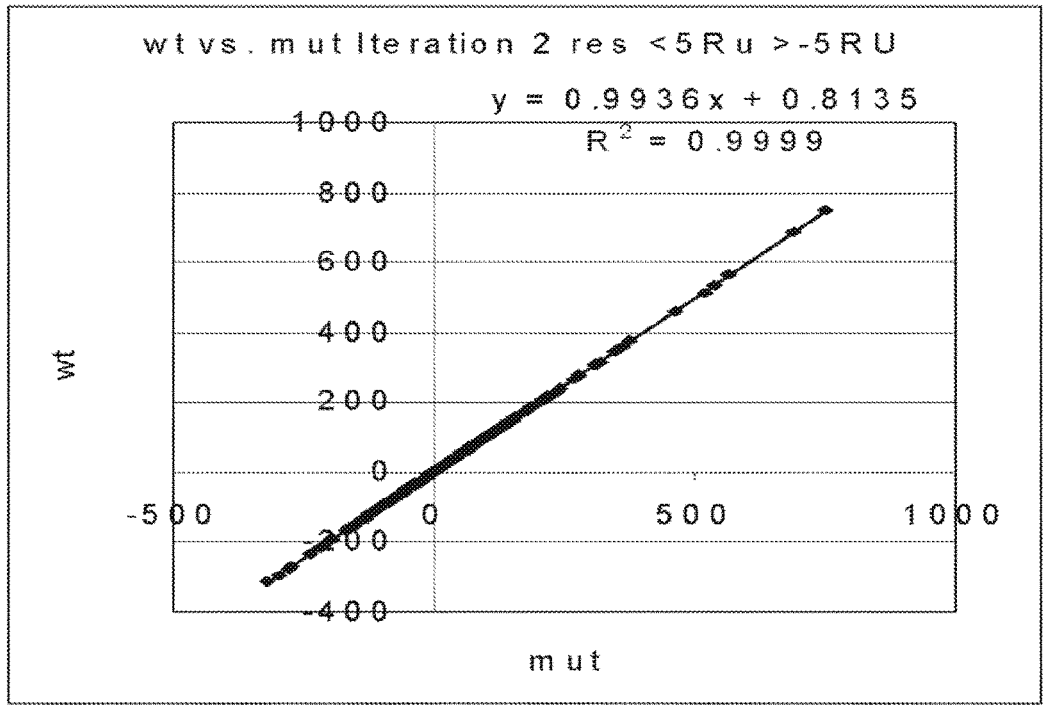
Figure 2:
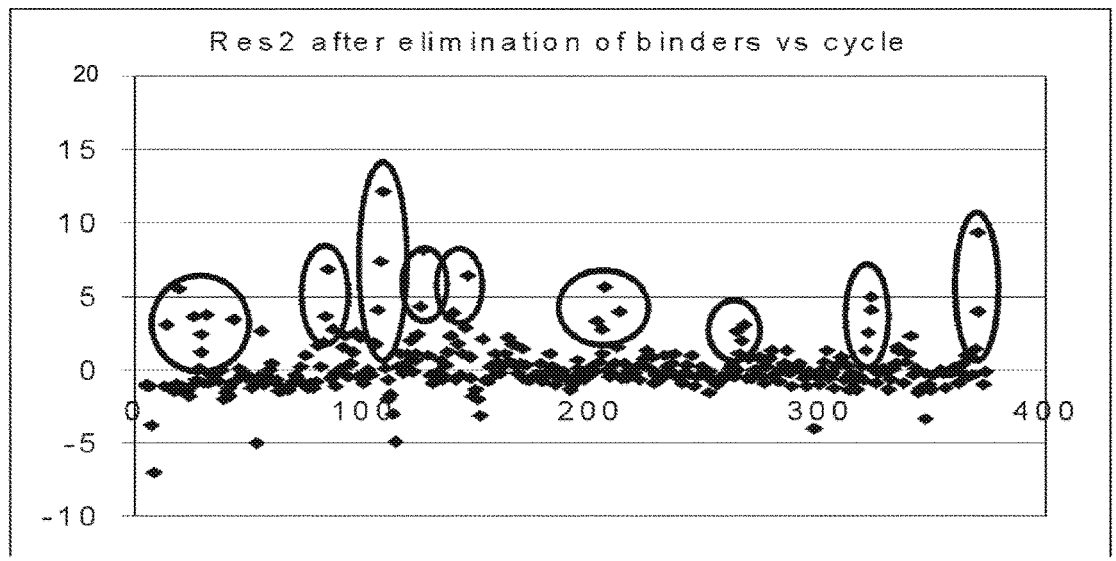
Figure 2E:
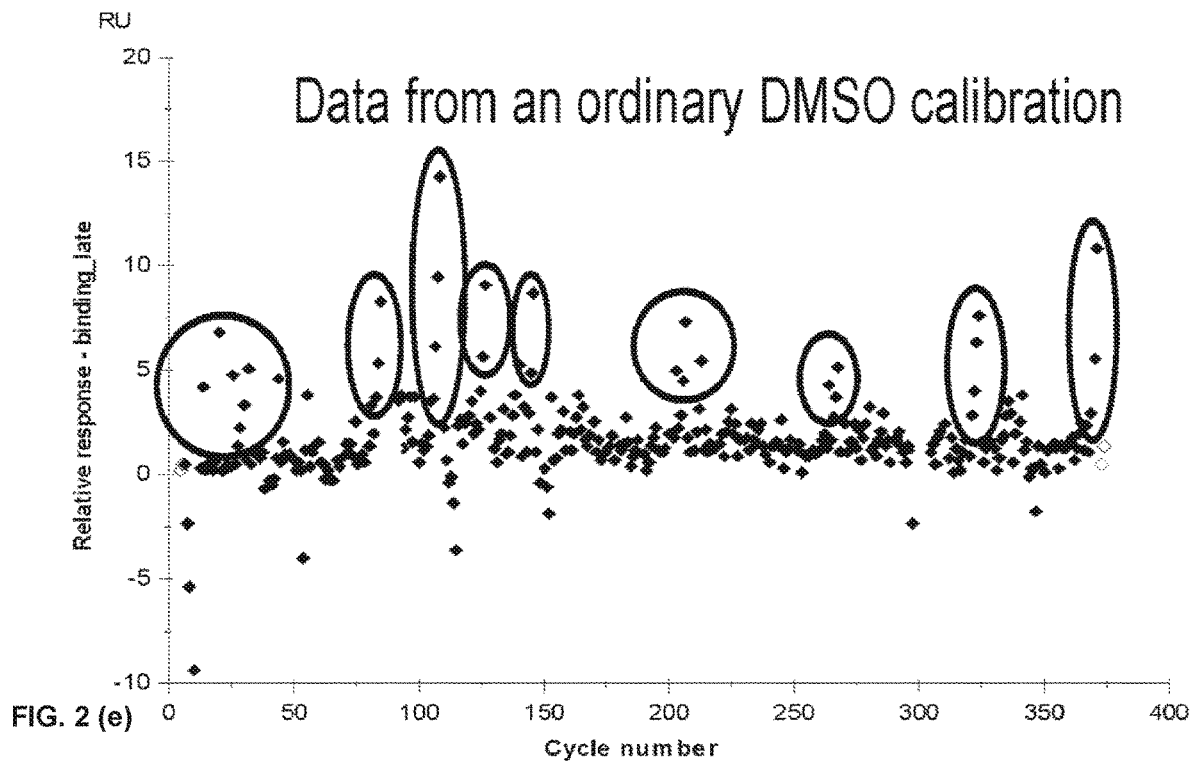
Figure 2F:
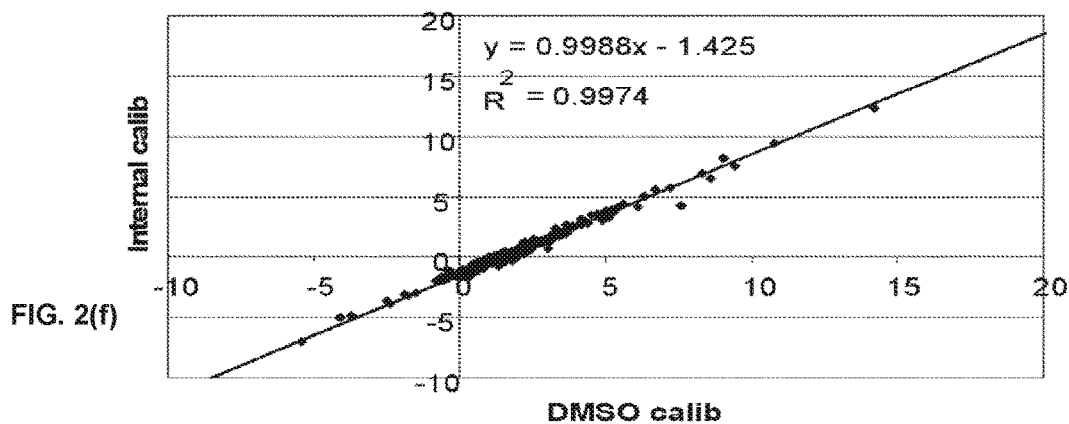

A simple linear model and a 5 RU fixed hit identification threshold were used for modelling the bulk-RI relationship between the target and the reference spot. With reference to FIG. 2, and first specifically to diagram (a) therein, a linear regression model (y=ax+b) was calculated between the target spot (wt) and the reference spot (mut). DAPA is the positive control. Diagram (b) shows the residuals between the calculated wt and the measured wt signal plotted as a function of sample cycle.

Compounds having residuals larger than +/−5 RU were eliminated and a new regression model was calculated in diagram (c). The new model was used for the prediction of the wt signal for all samples (also the ones which were excluded from the model) and residuals were plotted vs. cycle in diagram (d). Here the graph is zoomed in, i.e. DAPA is outside the graph range. For comparison, diagram (e) shows the binding pattern produced using the same data with an ordinary DMSO calibration which is identical with the binding pattern in (d).

Diagram (f) shows the excellent correlation between the wt signal using "with-in sample based calibration" as described above and DMSO-calibration, demonstrating that the two methods give very similar results.

As can be seen from the diagrams in FIG. 2, the linear fit is statistically good already in the first step of the algorithm ($R2=0.9991$), and nearly perfect after the second step (0.9999) (diagram (c)). After two steps the results are nearly identical with an ordinary DMSO calibration, as shown by diagrams (d)-(f).

Example 2

Use of Linear Fit in a Non-Linear Situation

In many cases the data may often seem "visually" and statistically ($R2>0.999$) to fit into a linear model even if the relationship is slightly non-linear. If there many binders, a large bulk-RI range is covered and the relationship is slightly non-linear the fit will be worse. This is demonstrated by FIG. 3 which illustrates the shortcomings of using a linear fit in a non-linear situation.

Figure 3:
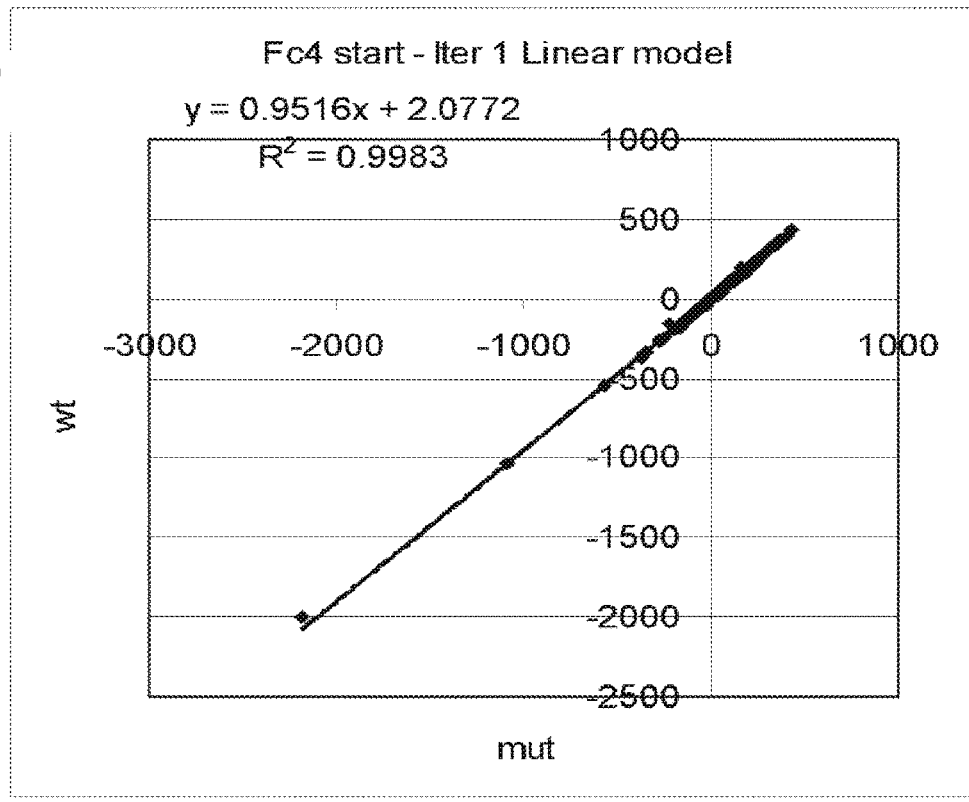
FIG. 3 is set of diagrams (a) to (f) showing results obtained when a linear model is used in a non-linear situation. Diagram (a) is a plot of target vs. reference spot after the first fitting to the model using all samples, and (b) is a corresponding residual plot. Diagram (c) is a plot of target vs. reference spot after the third fitting, (d) is the corresponding residual vs. cycle plot, and (e) shows the corresponding data obtained with an ordinary DMSO calibration. Diagram (f) is a plot of residuals after the third fitting vs. bulk-RI signal from the reference spot.
Figure 3:
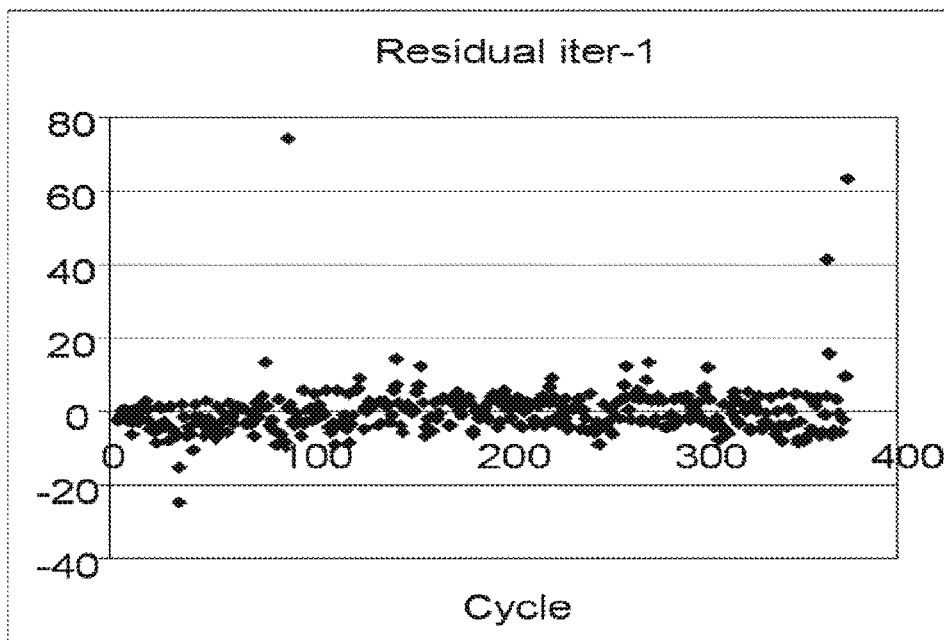
Figure 3:
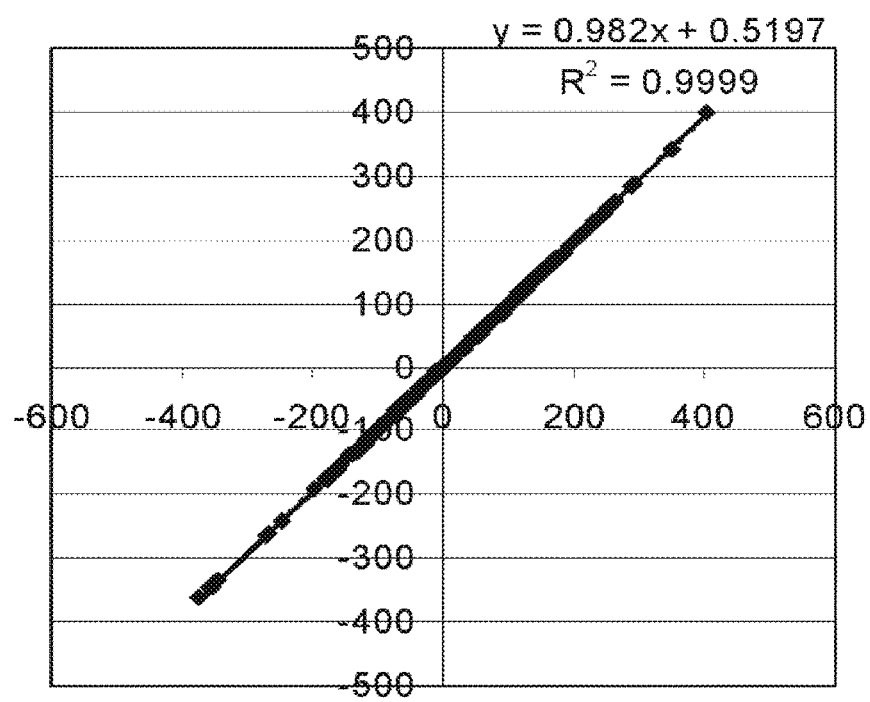
Figure 3:
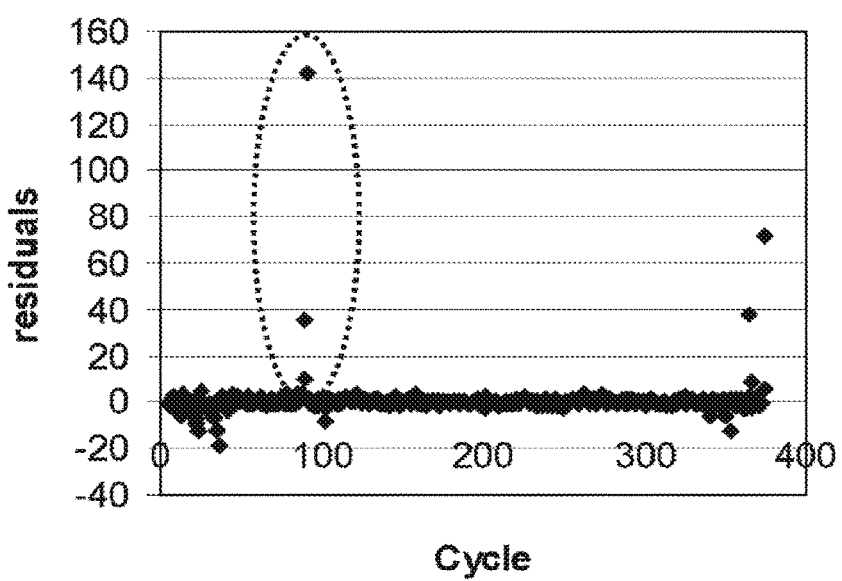
Figure 3:
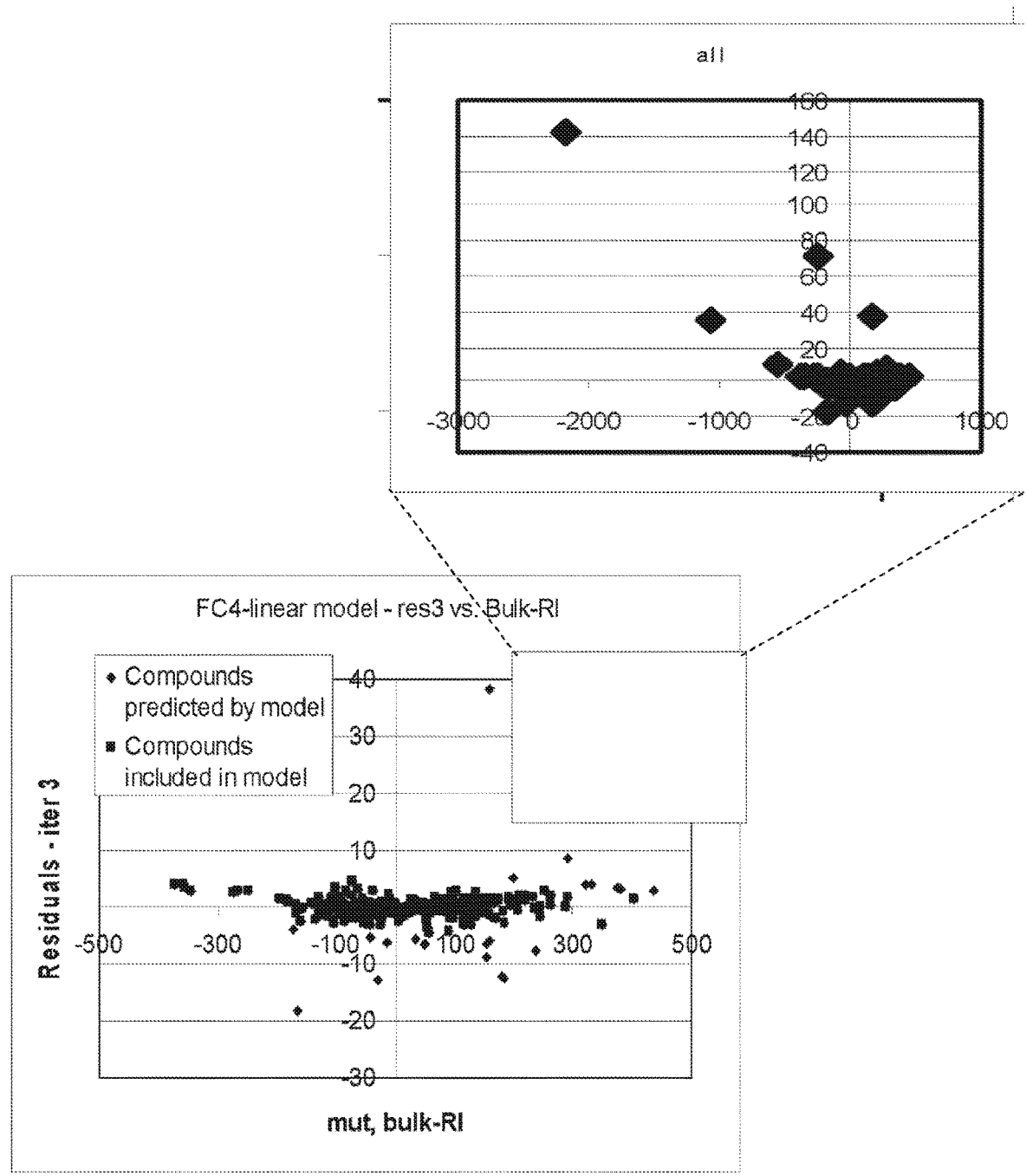
Figure 3:
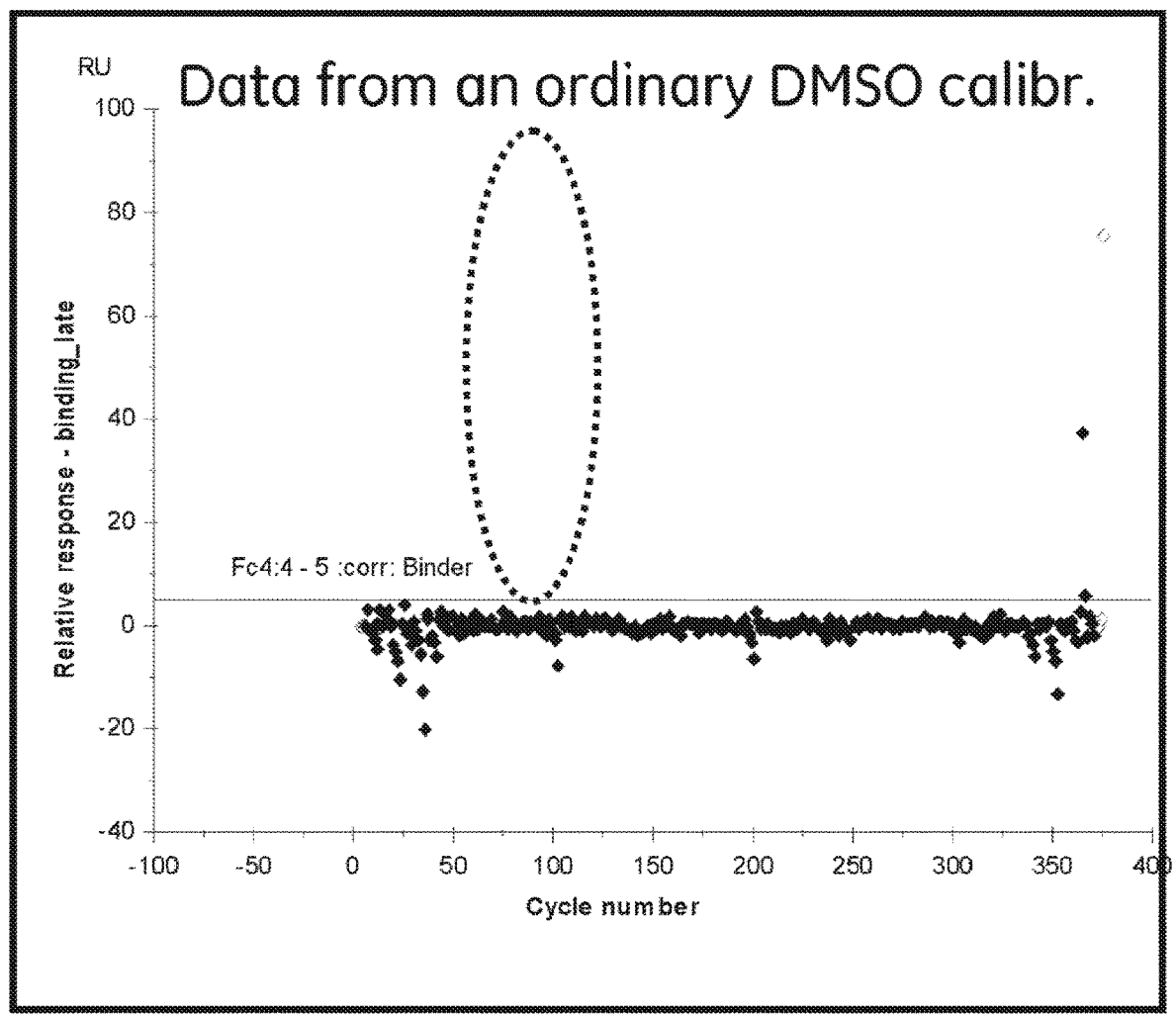

Diagram (a) in FIG. 3 is a scatter plot of target (wt) vs. reference (mutant) and the resulting linear model, and diagram (b) shows the residuals between the model and the measured signal.

Diagram (c) is a scatter plot after the third iteration of the algorithm (compound with residuals>+/−5 RU eliminated), and (d) shows residuals plotted vs. cycle. It is noted that in diagram c) the bulk range has shrinked to +/−400 RU and the compounds with high negative bulks now appear to have very large residuals in diagram (d). Diagram (e) shows data from an ordinary DMSO bulk calibration.

In diagram (f), residuals after the third step are plotted vs. bulk-RI signal from reference spot. It is noted that there is a non-even distribution of the residuals, i.e. all compounds with bulks in the −200 to −400 bulk range and the majority with bulk>300 have positive residuals. This indicates that a linear model is not adequate to model the bulk-RI.

As demonstrated above, diagrams (a)-(b) of FIG. 3 show a non-linear relationship where a linear model is inadequate and where compounds with large bulk RI-effects automatically will be interpreted as binders. These situations will also result in a "shrinkage" effect where compounds with large absolute bulk effects will automatically be identified as binders and eliminated from the bulk-RI model. While, as apparent from diagram (b) of FIG. 3, the resulting final fit is seemingly statistically sound ($R2=0.9999$) but the identified binders will deviate from an ordinary DMSO calibration, as shown in diagrams (d) and (f). Even if the compounds with the largest bulks are eliminated and the fit is statistically good, the non-linearity (in this shrinked bulk-RI range) can still be identified from a non-even distribution of the residuals vs. bulk-RI plot shown in diagram (f) of FIG. 3.

Example 3

Comparison of Linear and Quadratic Models and Illustration of Leverage Effect

A combination of a large bulk-RI and non-linearities will often give leverage effects which in turn give rise to larger residuals ($R2<0.99$) and non-binders will erroneously be classified as binders if linear models are used. This is demonstrated in FIG. 4 which uses the same data as in FIG. 3.

Figure 4:
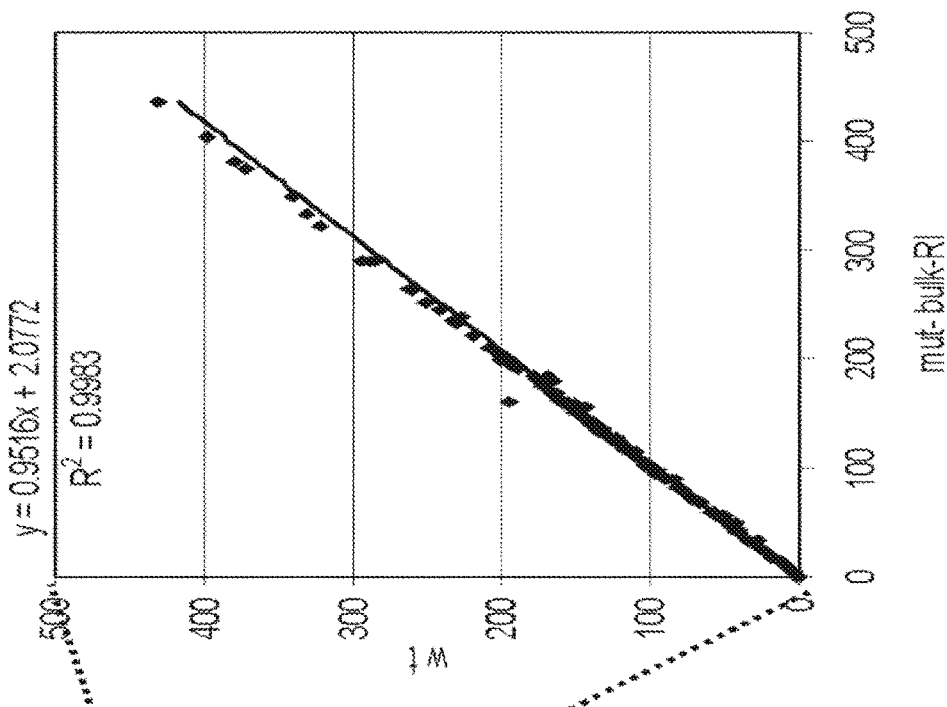
FIG. 4 is a set of diagrams (a) to (f) showing a comparison of the use of linear and quadratic models in the algorithm outlined in FIG. 1. Diagram (a) is a plot of target vs. reference spot after the first fitting to the model using all samples, (b) shows a zoomed-in area of (a) with a bad fit, and (c) and (d) are corresponding plots for a quadratic model. Diagram (e) is plot of residuals vs. bulk-RI signal for a quadratic model, and (f) is a corresponding plot of residuals vs. cycle no.
Figure 4:
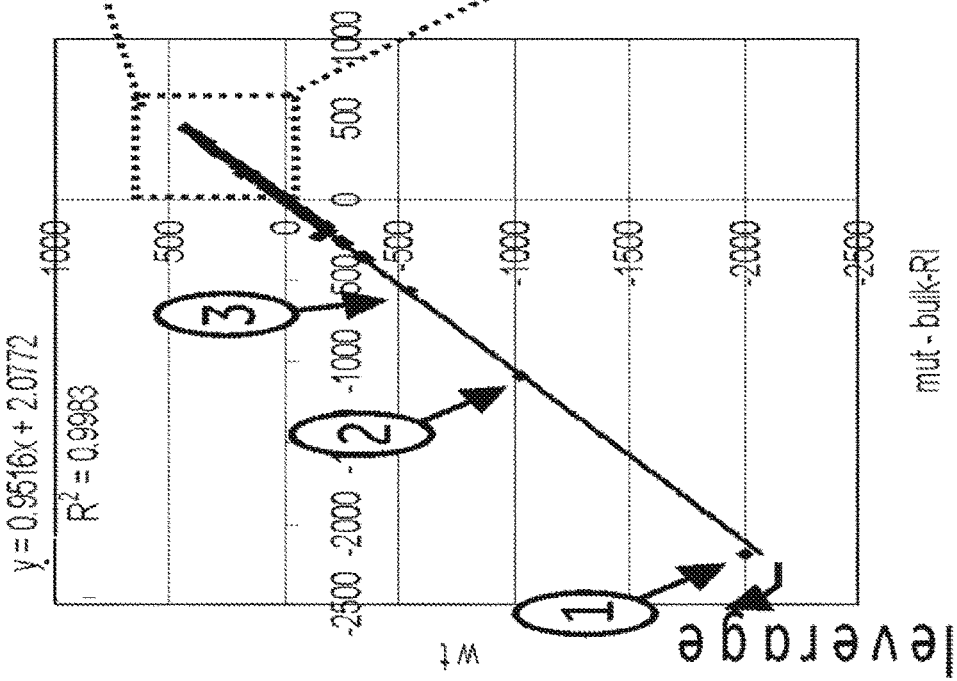
Figure 4:
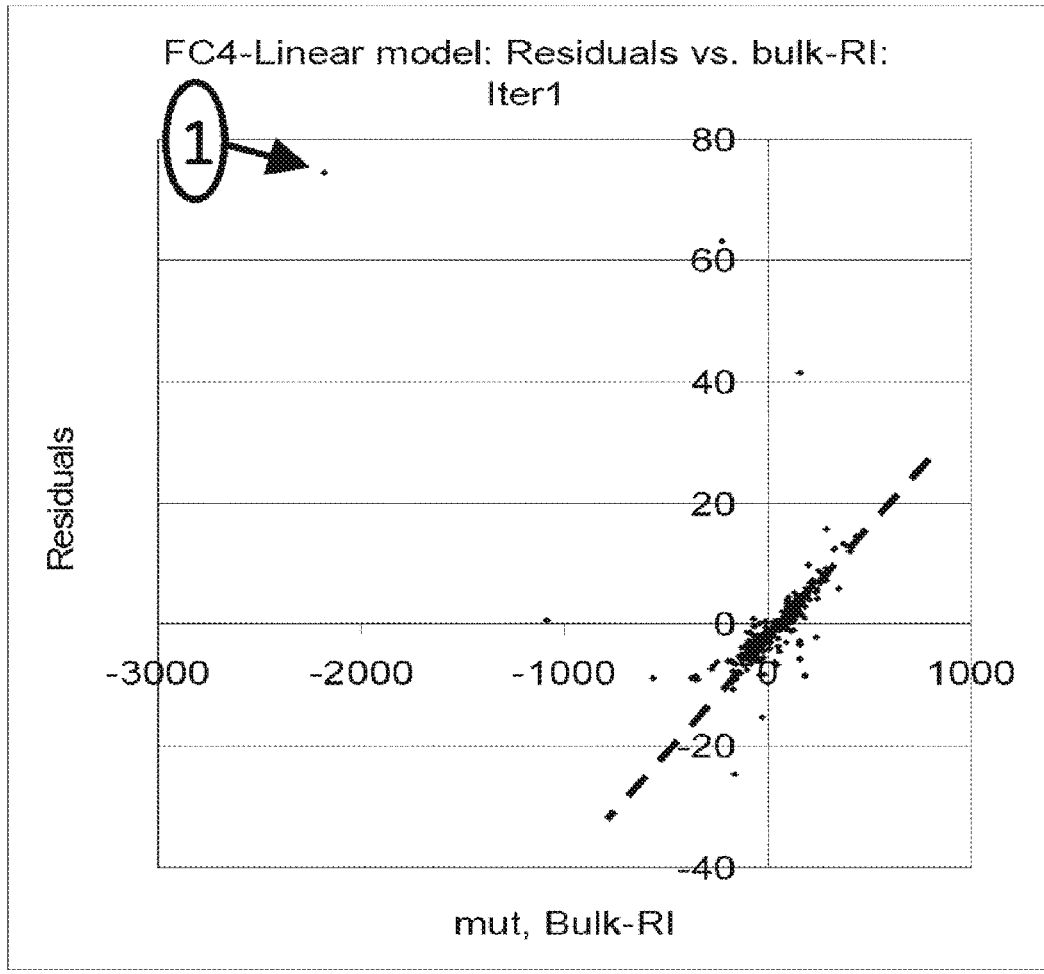
Figure 4:
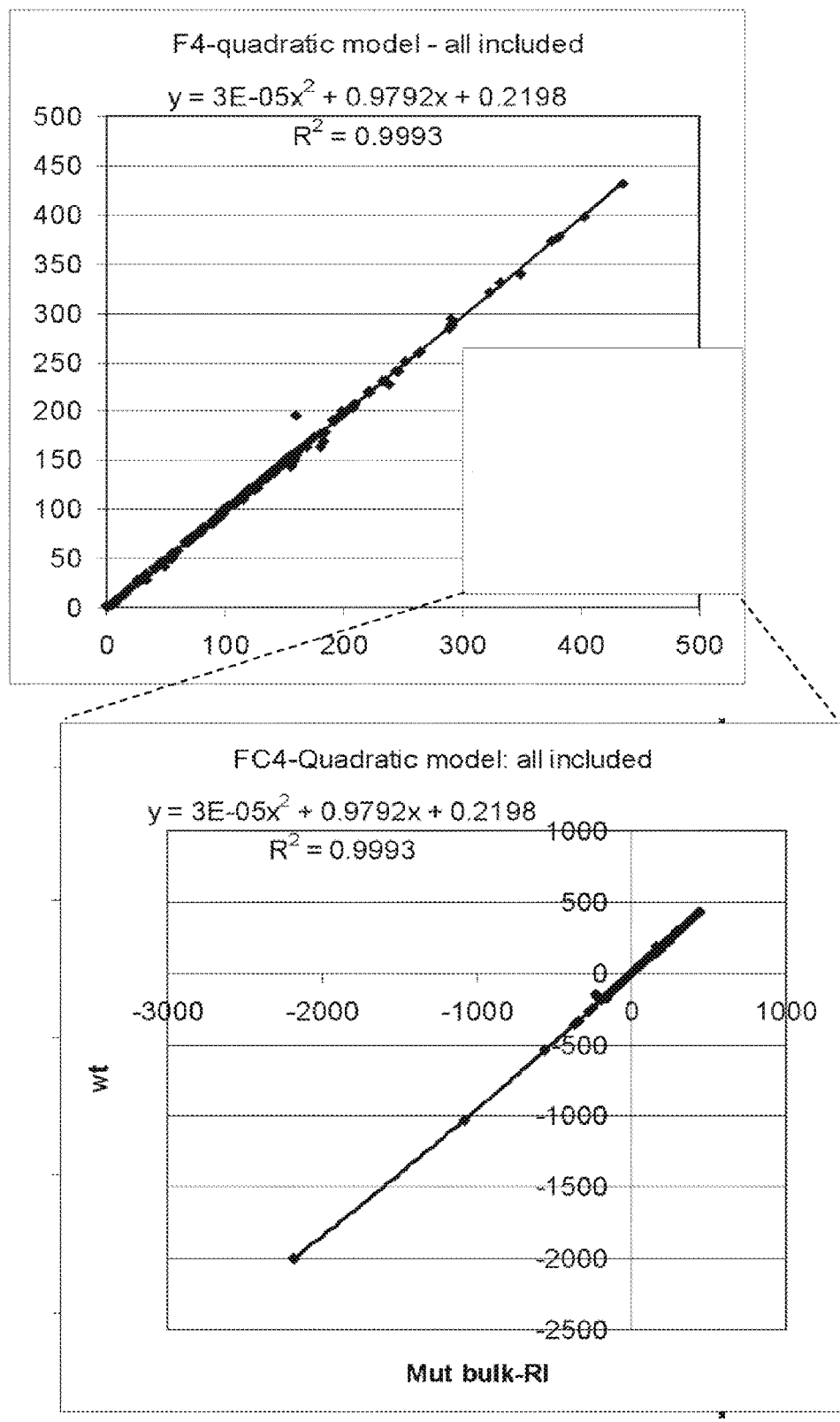
Figure 4:
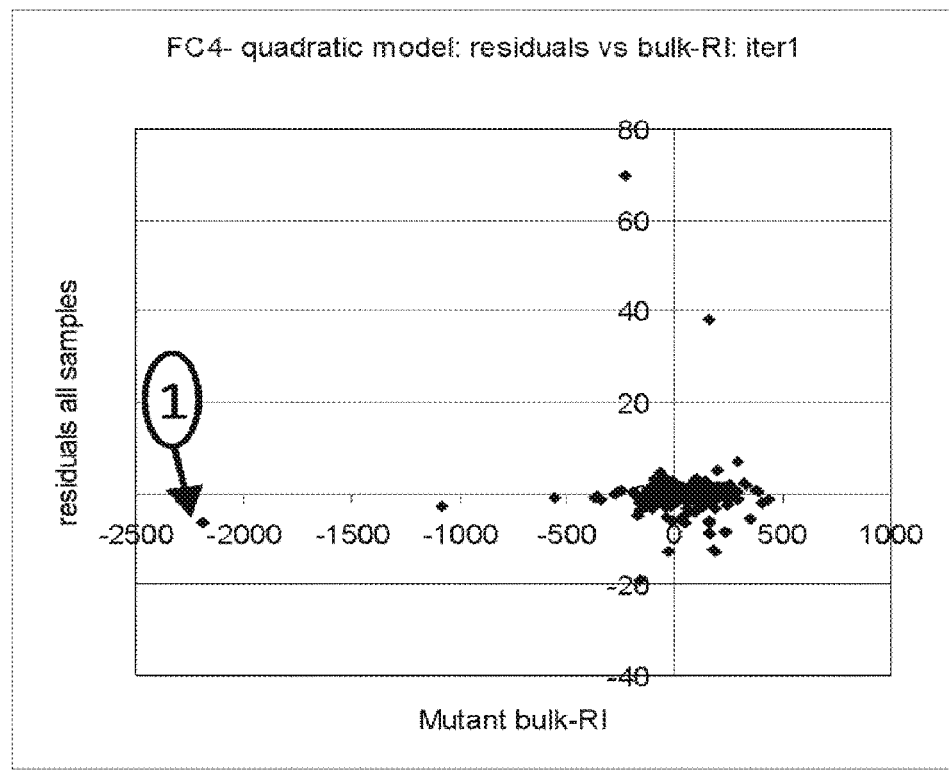
Figure 4:
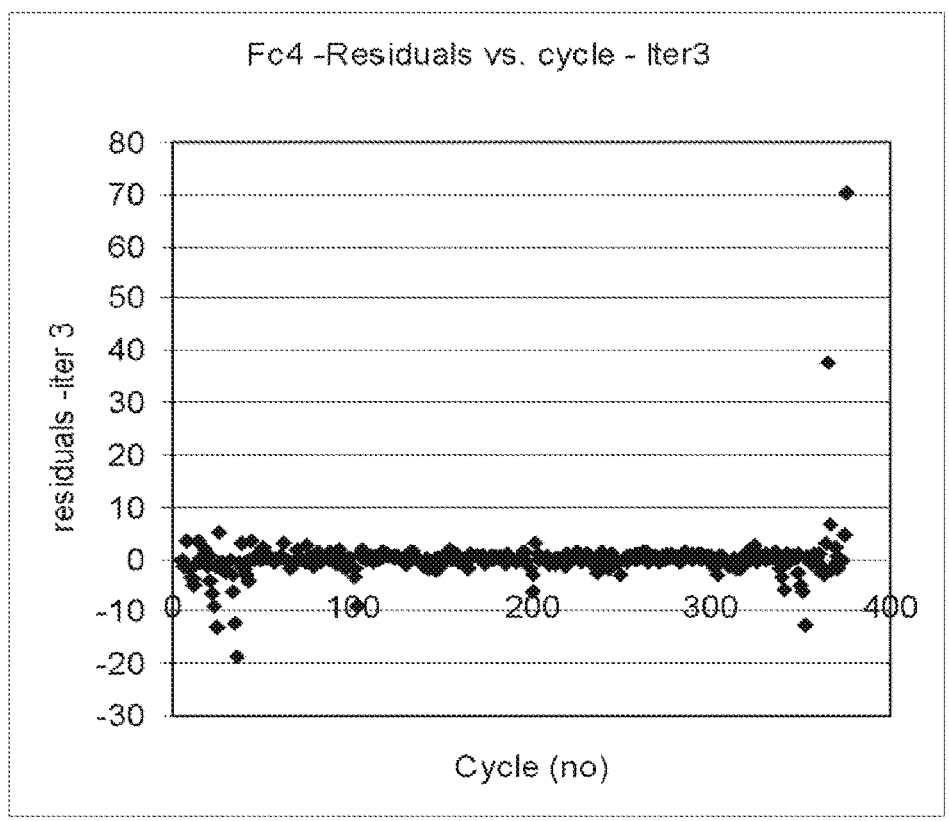

Diagram (a) in FIG. 4 shows a linear fit and regression model, and diagram (b) shows a zoomed-in area of diagram (a) with bad fit due to the leverage effect of the compounds with bad fit in the negative bulk-RI area.

As demonstrated by diagram (c), the limitations of the linear model can easily be identified by analysing the relation between the bulk-RI signal and the residuals. With a proper model no correlation should exist between the residuals and the bulk-RI signal. The residuals from the first step can thus be used for identification of non-linearities.

Diagram (d) shows a quadratic fit showing the same (zoomed-in) area as in diagram (b), diagram (e) shows a corresponding plot to diagram (c), and the corresponding residual plot is shown in diagram (f). As apparent therefrom, the quadratic model gives a much better fit, the residuals are evenly distributed and, as seen in diagram (f), the false positives seen in diagram (d) of FIG. 3 are now eliminated.

Example 4

Cycle Based Sequential Modelling of Bulk-RI Effect

In runs with rapidly bleeding target and/or runs with many cycles a significant variation in the bulk-RI elimination model over time (e.g. beginning and end of run) may be obtained. This was initially identified as systematic zero binding levels in residuals vs. cycle plots. With reference to, for example, diagram (d) of FIG. 2 discussed above, all the non-binding compounds in the first 20 cycles have negative signals (a few RU's). In that case, a single global model based on all the about 360 cycles was used for the modelling of the bulk-RI. To visualise the need for cycle based sequential modelling of the bulk-RI models, a 42 hours long 637 cycle run (sample preparation made with a robot) was analysed where the samples were arbitrary divided into two groups, cycles 1-299 and cycles 300-637, respectively. Corresponding target signal vs. bulk-RI plots are shown in FIG. 5, where the 1-299 cycles and 300-637 are displayed with separate symbols and the bulk-RI was modelled with separate models for the two groups.

Figure 5:
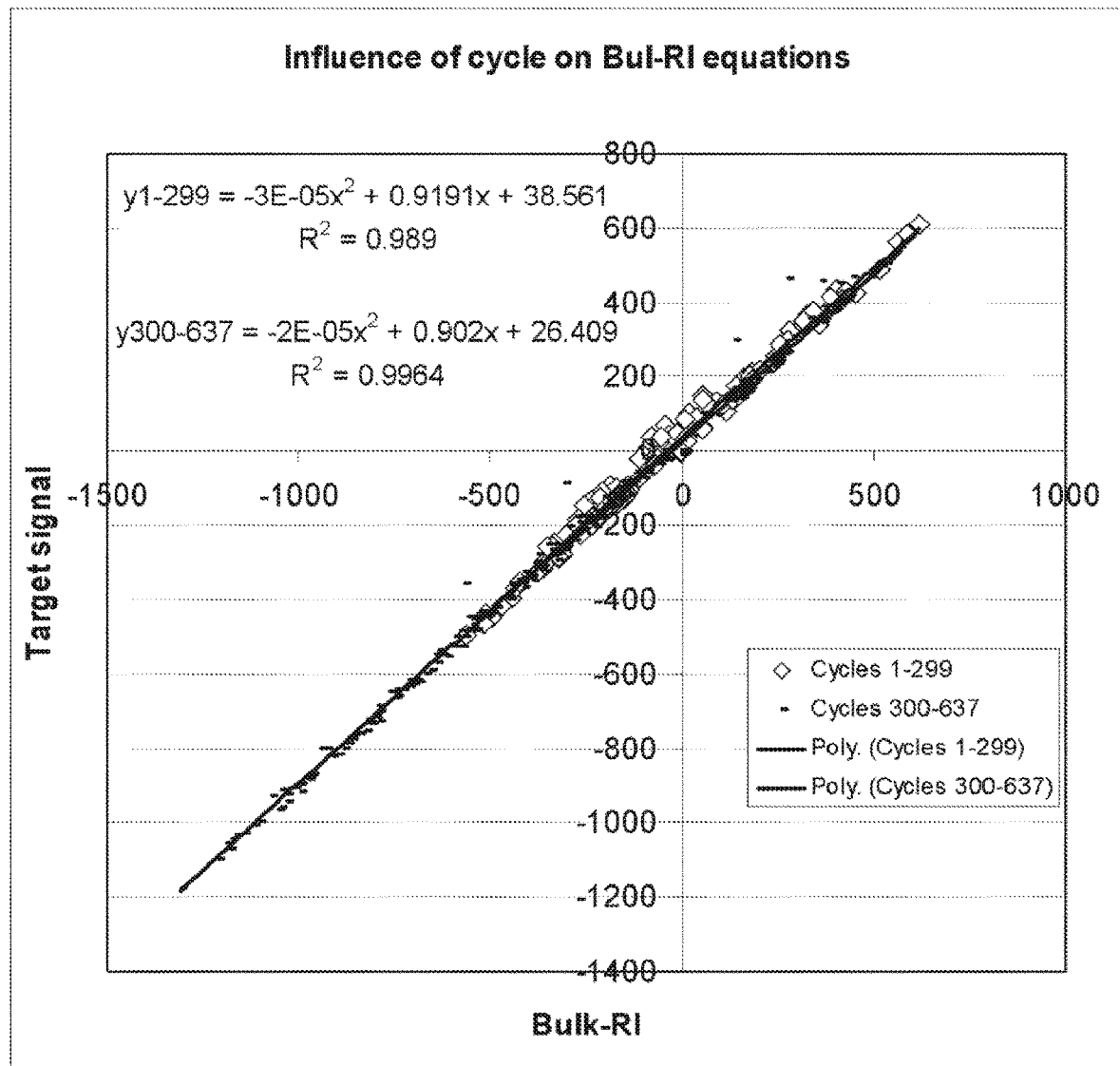
FIG. 5 is diagram showing target signal vs. bulk-RI signal for a plurality of sample screen cycles divided into two groups, cycles 1-299 and 300-637, respectively.

As can be seen in FIG. 5, the bulk-RI range is significantly different for the two sets and the higher range for the 300-637 group indicates e.g. evaporation. The two bulk-RI models also are significantly different, i.e. the intercept is has a difference of ~12 RU. (26.4 and 38.6).

Example 5

Identification of Binders Based on Statistics

In the examples above, the identification of binders was based on experienced based rule-of-thumb type of thresholds ending up in final 3-5 RU's hit identification thresholds for Sensor Chip CM5 surfaces (GE Healthcare). Since the background noise varies in different screens more scientifically stringent, user friendly and automatic selection of hits and elimination of these from the bulk-RI model would be needed.

Figure 6:
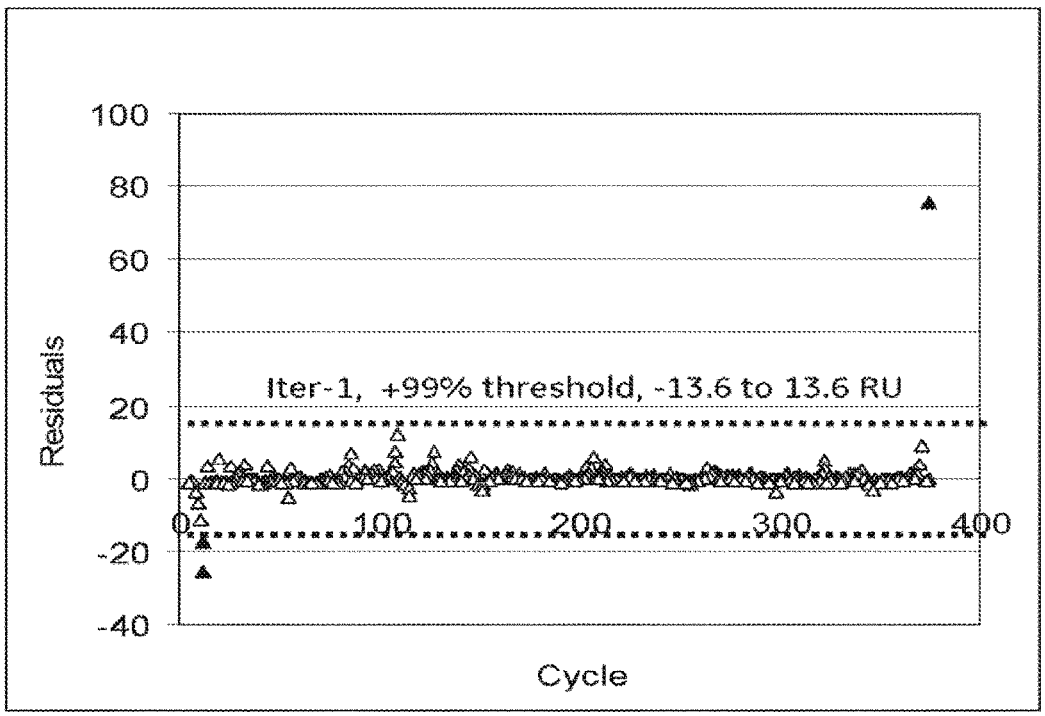
FIG. 6 is a set of diagrams (a) to (d) showing plots of residuals vs. cycle no. after different steps in an iterative fitting procedure with statistical thresholds. Diagram (a) is a residual plot after the first fitting, (b) after the second fitting, (c) after the third fitting, and (d) after the fourth and fifth fittings.
Figure 6:
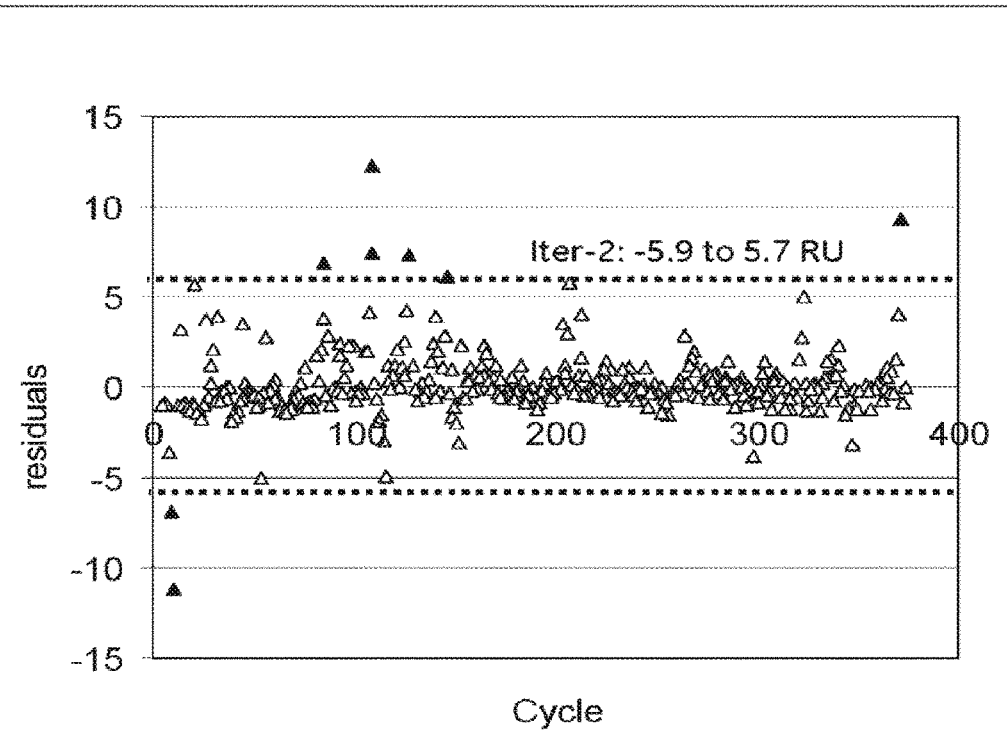
Figure 6:
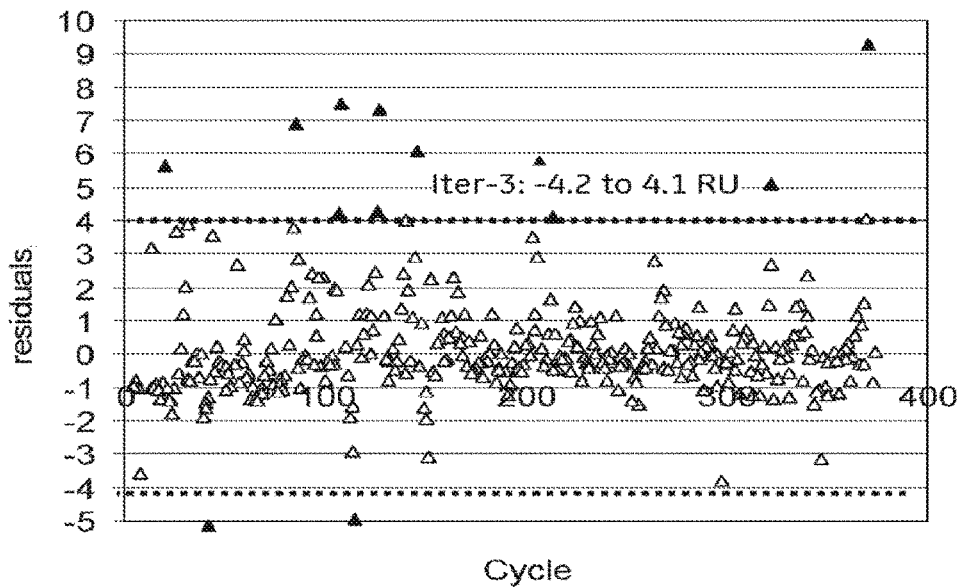
Figure 6:
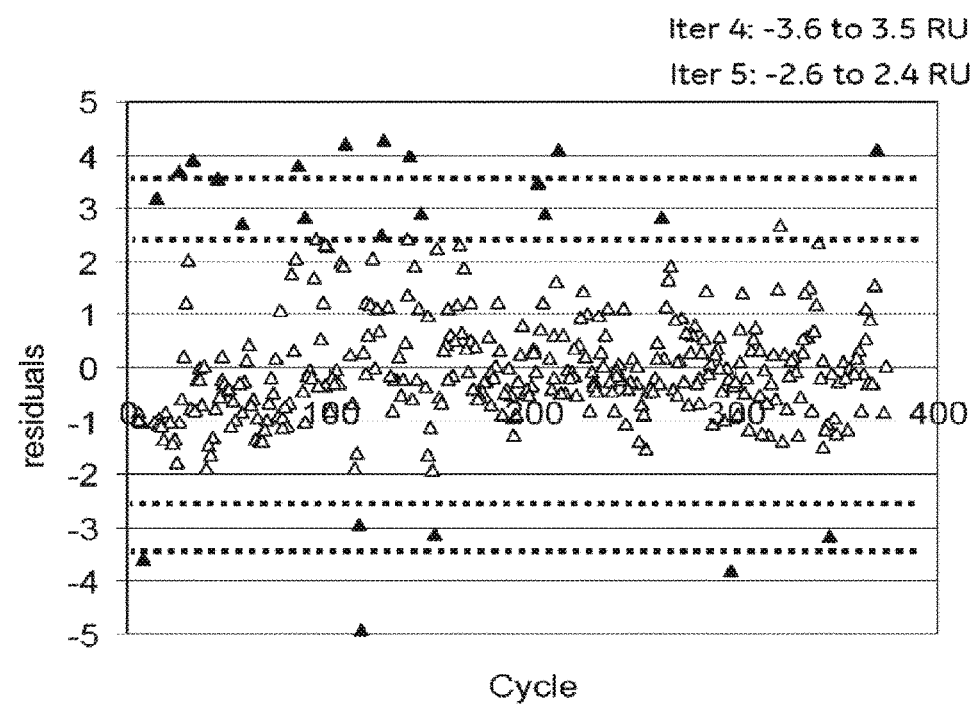

FIG. 6 illustrates the application of a common simple outlier detection statistics used for identification of binders, involving an evolving stepwise statistical threshold for the identification and elimination of binders followed by refitting of new calibration models.

In diagram (a) residuals are plotted vs. cycle after the first step of the algorithm using a quadratic model. The calculated 99% outlier threshold, i.e. hit identification threshold, was calculated as average residuals+3*SD and displayed as a dotted line. The negative threshold (average residuals−3*SD) indicated compounds binding stronger to the reference spot in comparison with the target spot. The three marked compounds outside the thresholds were identified as the first set of binders. The high 13.6 RU's in threshold is due to the inclusion of all compounds to the model (first step).

Diagram (b) in FIG. 6 shows the residuals vs. cycle of a new model after the binders in (a) were eliminated and a new bulk calibration model was calculated. The threshold displayed is now based on the SD after elimination of the 3 compounds, and has rapidly decreased to ~6 RU.

Diagrams (c) and (d) show the increased number of compounds identified after the third to fifth iterations. After five iterations the threshold has thus decreased to ~2.5 RU and the majority of binders are identified as hits.

The Examples above demonstrate that when a vast majority of the compounds in a screen are non-binders, these compounds can be used for the calibration and elimination of the bulk-RI effect originating mainly from small variations in DMSO content of the samples. It is also shown that the relationship between the reference and target surface often is non-linear, and a quadratic or other type of non-linear model should therefore preferably be used.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A method of identifying screening hits of one or more low molecular weight binders in a plurality of fluid samples, the one or more low molecular weight binders are capable of specifically binding to a binding partner immobilized on a sensing surface of a biosensor, the method comprising:
   providing the plurality of fluid samples comprising the one or more low molecular weight binders and a non-binder, wherein the presence of the non-binder gives rise to a varying effect not correlated with specific binding and results in a higher reference sensing surface response than those of the one or more low molecular weight binders;
   contacting each of the plurality of fluid samples with a target sensing surface having the binding partner immobilized thereto and a reference sensing surface;
   detecting an interaction between each of the fluid samples and the target sensing surface and the reference sensing surface to generate a plurality of sensing surface responses, wherein the plurality of sensing surface responses comprises a target sensing surface response (y) and a corresponding reference sensing surface response (x) for each of the fluid samples; and
   subjecting the plurality of sensing surface responses to an iterative process for removing the varying effect not correlated with specific binding, without creating a calibration curve for solvent correction, the iterative process comprising:
      fitting the plurality of sensing surface responses to a regression model $y=f(x)$ which defines a relationship between the target sensing surface response (y) and the corresponding reference sensing surface response (x), wherein the regression model is selected from a linear or a non-linear regression model;
      calculating a residual for each of the fitted plurality of sensing surface responses;

removing each of the sensing surface responses whose residual is above a positive threshold value from the plurality of sensing surface responses;

repeating the fitting, calculating, and removing steps until the regression model at least substantially converges, wherein the substantially converged regression model describes the varying effect not correlated with specific binding; and identifying the presence of the one or more low molecular weight binders by each of the sensing surface responses whose residual is above the positive threshold value.

2. The method of claim 1, wherein the subjecting further comprises removing each of the sensing surface responses whose residual is below a negative threshold value from the plurality of sensing surface responses, and wherein each of the sensing surface responses removed for having residuals below the negative threshold value indicates that the corresponding fluid samples have a species that binds the reference sensing surface.

3. The method of claim 1, wherein the at least substantially converged regression model defines a non-specific bulk effect.

4. The method of claim 3, wherein the non-binder giving rise to the non-specific bulk effect is a solvent.

5. The method of claim 4, wherein the solvent comprises DMSO.

6. The method of claim 3, wherein said non-specific bulk effect is a bulk refractive index effect.

7. The method of claim 1, wherein the reference surface is selected from a) a surface without an immobilized binding partner, and b) a surface comprising an immobilized binding partner, the binding site of which has been blocked.

8. The method of claim 1, wherein the regression model is quadratic.

9. The method of claim 1, wherein said positive threshold value is a statistical threshold value.

10. The method of claim 1, wherein the plurality of sensing surface responses from the detection step are divided into at least two groups, and wherein each group is used in a separate subjecting that utilizes separate fitting processes using separate regression models.

11. The method of claim 1, wherein a sensor based on mass-sensing is used.

12. The method of claim 1, wherein the subjecting is computer-implemented.

13. The method of claim 1, wherein a sensor based on surface plasmon resonance (SPR) is used.

14. The method of claim 1, wherein the varying effect comprises a non-specific bulk effect, and removing the varying effect and identifying the presence of the one or more low molecular weight binders capable of specifically binding the binding partner is performed simultaneously during the iterative process.

15. The method of claim 1, wherein the method does not require a calibration using a calibration solution of the non-binder.

16. A non-transitory computer program product comprising:

a computer; and memory storing instructions, which, when executed, cause the a computer to identify screening hits of one or more low molecular weight binders in a plurality of fluid samples, the one or more low molecular weight binders capable of specifically binding to a binding partner immobilized on a sensing surface of a biosensor, by at least:

providing the plurality of fluid samples including the one or more low molecular weight binders and a non-binder, wherein the presence of the non-binder gives rise to a varying effect not correlated with specific binding and results in a higher reference sensing surface response than those of the one or more low molecular weight binders;

contacting each of the plurality of fluid samples with a target sensing surface having the binding partner immobilized thereto and a reference sensing surface;

detecting an interaction between each of the fluid samples and the target sensing surface and the reference sensing surface to generate a plurality of sensing surface responses, wherein the plurality of sensing surface responses comprises a target sensing surface response (y) and a corresponding reference sensing surface response (x) for each of the fluid samples; and subjecting the plurality of sensing surface responses to an iterative process for removing the varying effect not correlated with specific binding, without creating a calibration curve for solvent correction, the iterative process including:

fitting the plurality of sensing surface responses to a regression model y=f(x) which defines a relationship between the target sensing surface response (y) and the corresponding reference sensing surface response (x), wherein the regression model is selected from a linear or a non-linear regression model;

calculating a residual for each of the fitted plurality of sensing surface responses;

removing each of the sensing surface responses whose residual is above a positive threshold value from the plurality of sensing surface responses;

repeating the fitting, calculating, and removing steps until the regression model at least substantially converges, wherein the substantially converged regression model describes the varying effect not correlated with specific binding; and identifying the presence of the one or more low molecular weight binders by each of the sensing surface responses whose residual is above the positive threshold value.

* * * * *